United States Patent
Schrayer

(10) Patent No.: US 6,575,887 B1
(45) Date of Patent: Jun. 10, 2003

(54) DEVICES FOR THE INHIBITION OR SUPPRESSION OF CELLULAR PROLIFERATION IN TUBULAR BODY STRUCTURES

(75) Inventor: Howard L. Schrayer, Princeton, NJ (US)

(73) Assignee: Epsilon Medical, Inc., Princeton, NJ (US)

( * ) Notice: Subject to any disclaimer, the term of this patent is extended or adjusted under 35 U.S.C. 154(b) by 92 days.

(21) Appl. No.: 09/715,831

(22) Filed: Nov. 17, 2000

(51) Int. Cl.[7] ................................. A61N 5/00
(52) U.S. Cl. .......................................... 600/3
(58) Field of Search ..................... 600/1–8; 604/19, 604/53, 104, 106, 202

(56) References Cited

U.S. PATENT DOCUMENTS

| | | |
|---|---|---|
| 4,733,665 A | 3/1988 | Palmaz |
| 4,754,745 A | 7/1988 | Horowitz |
| 4,946,435 A | 8/1990 | Suthanthiran et al. |
| 5,030,195 A | 7/1991 | Nardi |
| 5,059,166 A | 10/1991 | Fischell et al. |
| 5,302,168 A | 4/1994 | Hess |
| 5,322,499 A | 6/1994 | Liprie |
| 5,342,283 A | 8/1994 | Good |
| 5,540,659 A | 7/1996 | Teirstein |
| 5,871,708 A | 2/1999 | Park et al. |
| 5,873,811 A | 2/1999 | Wang et al. |
| 5,897,573 A | 4/1999 | Rosenthal et al. |
| 6,287,249 B1 * | 9/2001 | Tam et al. .................. 600/3 |
| 6,296,603 B1 * | 10/2001 | Turnlund et al. ............. 600/3 |
| 6,350,226 B1 * | 2/2002 | Fischell et al. .............. 600/1 |

OTHER PUBLICATIONS

Palder SR, Kirkman RL, Whittemore AD et al., *Vascular Access for Hemodialysis*, Ann Surg., 1995, 202: 235–239.

Bethard GA, *Mechanical Versus Pharmacomechanical Thrombolysis for the Treatment of Thrombosis of Dialysis Access Grafts*, Kidney Int., 1994; 45: 1401–1406.

Smouse, *Strategies in the Treatment of the Failing Hemodialysis Graft*, Midwest Institute for Interventional Therapy—http://www.mitt.com/smouse.htm.

* cited by examiner

*Primary Examiner*—Melvin Jones
(74) *Attorney, Agent, or Firm*—Woodbridge & Associates, P.C.; Richard C. Woodbridge; Stuart H. Nissim

(57) ABSTRACT

A surgically implantable radioactive wrap is positioned around the wall of a body vessel, duct or passageway to maintain patency of these structures by mitigating overexuberant cellular proliferation. Such excessive cellular growth may occur as the result of a disease process or following a trauma or an intentional surgical or intravascular intervention. The device provides for delivery of ionizing radiation to a localized target tissue site. Integral design features provide for the shielding of non-targeted tissues and for the attachment of the device to the target tissue structure. A radiation attenuation element serves to absorb extraneous low-energy electrons incidentally emitted by the treatment source and provides for a more uniform radiation dose distribution through the full thickness of the target tissues. The wrap can be easily applied with minimal handling and with limited radiation exposure to operating personnel.

18 Claims, 4 Drawing Sheets

DEVICES FOR THE INHIBITION OR SUPPRESSION OF CELLULAR PROLIFERATION IN TUBULAR BODY STRUCTURES

FIELD OF THE INVENTION

This invention relates to a surgical implant for the localized application of radiation therapy, more particularly to a surgical implant intended for the prophylactic treatment or the mitigation of partial or total blockages in vessels, body ducts or other tubular body structures.

DESCRIPTION OF THE RELATED ART

A number of medical problems are the result of overexuberant cellular proliferation in tubular body structures. A large proportion of end-stage renal disease (ESRD) patients use an implanted synthetic vascular graft to provide vascular access for dialysis treatment. Palder S R, Kirkman R L, Whittemore A D, et al., Vascular Access for Hemodialysis. Patency Rates and Results of Revision., Ann. Surg., 1995; 202: 235–239, discussed that these grafts typically fail in 14–19 months with a reported primary occlusion rate of 15–50% at one year. Bethard G A, Mechanical Versus Pharmacomechanical Thrombolysis for the Treatment of Thrombosis of Dialysis Access Grafts, Kidney Int., 1994; 45: 1401–1406, demonstrated clinically that, most graft failures result from thrombosis (80–90%); and in turn, the thrombosis is typically caused by a low flow condition, most frequently (>90%) stenosis at the graft/vein anastomosis. The stenosis is the result of an overexuberant cellular proliferation that has been observed following other vascular interventions including angioplasty and synthetic graft placement. It is this failure rate, and the attendant need to repair or replace the vascular access that generate the high costs and hospitalization rates associated with the management of the ESRD patient.

A similar intimal hyperplasia phenomenon has prevented the adoption of small diameter synthetic vascular grafts for use in coronary artery bypass surgery. Other conditions requiring treatment include the growth or regrowth of tumor tissues on or adjacent to body vessels, ducts and passageways.

To date, approaches to removing narrowings and blockages from body passageways have been both mechanical and pharmacological. Although many of these treatments are successful in the immediate goal of restoring flow through the duct or vessel, they do not always treat the underlying cause of the stenosis; and reclosure may occur after a short period. Treatments that involve various medical devices include balloon angioplasty, embolectomy, surgical excision or by-pass, clot aspiration and intravascular stent implantation. In contradistinction to the present invention, most of these interventions are typically undertaken to treat an existing stenosis and not as prophylactic or preventative treatments. As such, they present the risks of a secondary surgical procedure in addition to the risks and potential adverse reactions associated with the primary procedure.

Pharmocologic therapy includes the use of various "blood-thinners" or anti-thrombotic agents. These powerful drugs are not suitable for all patients and are associated with a high risk of complication related to uncontrollable bleeding. While these drugs can often dissolve newly formed clots, they are less effective in removing established thrombus and have no impact on the overexuberant cellular proliferation (intimal hyperplasia) which may be the root cause of the stenosis.

With the acknowledged inadequacy of current stenosis and restenosis prevention techniques, the medical community has initiated experimental studies with a variety of local radiation delivery devices. It has been well established that radiation therapy is of value in mitigating exuberant cellular proliferation as in the case of cancer radiotherapy. More recent investigations have demonstrated the potential usefulness of various intravascular radiation delivery devices; however, no devices or treatments have thus far been developed specifically for the purpose of localized delivery of radiotherapy to tubular body structures by means of a circumferential wrap.

Some relevant proposed treatment means define devices that can be prepared in the form of sheets or films that are intended for use in essentially planar form. U.S. Pat. No. 4,946,435, describes a film sealed in an envelope. The device is flexible and can be conformed to provide radiation treatment to irregular contours. This patent discloses a polymeric radiation carrier film enclosed in a polymeric envelope. The patent describes a laminated structure but does not disclose use of a radiation attenuation element adjacent to the radioactive surface. Liprie describes a continuous radioactive sheet in U.S. Pat. No. 5,322,499. This device is defined to have an iridium/platinum core that is more rigid than an outer sealing coating. This soft outer cover is designed to allow the radioactive sheet to be cut into smaller sealed segments, thus creating sizes and essentially planar shapes suited for a particular application. This patent does not disclose the use of either an integral shield to protect non-targeted tissues or a radiation attenuation element to provide for a more even radiation dose gradient. In U.S. Pat. No. 5,342,283. Good describes radioactive microspheres that can be used to coat flexible substrates for use in the treatment of disease. This patent also does not disclose the use of either an integral shield to protect non-targeted tissues or a radiation attenuation element to provide for a more even radiation dose gradient. Park et al. describe a radioactive patch/film in U.S. Pat. No. 5,871,708. This device is designed to treat various kinds of cancers and dermal disease and consists of a laminated structure in which the radiation layer is not integral to the carrier film. This patent does not describe either a shield or a radiation attenuation element. None of the above mentioned patents contemplate treatment of obstructions in tubular body structures.

Some of the proposed radioactive devices were designed to provide radiation treatment as adjunctive therapy to coronary angioplasty procedures. A majority of coronary angioplasty procedures have been augmented with the placement of intravascular stents. One such device is described in U.S. Pat. No. 4,733,655 et seq. by Palmaz. These devices have improved six-month restenosis rates from nearly 40% to approximately 25%. Stents have also been placed across the graft/vein junction of failed dialysis access grafts as part of the effort to reopen the stenosed or occluded access grafts. Probably because the stent is placed across the return flow of blood at the juncture of the graft and the natural vein, success has been limited; and 50% of the stented grafts reclose within six months. Radioactive stents are currently being clinically studied as a potential improvement to non-radioactive stent placement following coronary angioplasty. The application of radioactive stents is described in U.S. Pat. No. 5,059,166. Early results seem to support use of the radioactive stents in conjunction with angioplasty, and six-month restenosis rates of less than 15% are being reported. However, radioactive stents will also physically obstruct flow in dialysis grafts.

Alternate treatment approaches for coronary artery restenosis involve the use of radioactive catheters or wires as part of the angioplasty procedure. These devices also require the use of a vascular puncture for access; but unlike the stent, do not involve permanent implantation of a device. The catheter type devices position an array of radioactive seeds or pellets at the site of the angioplasty for several minutes following the balloon angioplasty procedure. One example of a catheter type device has been described in U.S. Pat. No. 5,540,659. These devices deliver a single exposure dose; and thus present a much higher radioactivity dose rate than a stent implant that delivers radiation over a much longer time. This factor has raised radiation safety issues. Because the normal healing process following graft placement is quite different from the healing process following angioplasty it is unlikely that a one-time treatment with a catheter or wire device would be effective for use in treating graft related stenosis.

Radioactive balloon catheters, similar to those used for angioplasty have also been evaluated for the treatment of stenosis following coronary angioplasty. An example of a balloon catheter that is intended to function in this manner has been described in U.S. Pat. No. 5,302,168 et seq. Some versions of the balloons are filled with a radioactive liquid or gas and other catheters incorporate radioactive material in the wall of the balloon. These balloons can only be inflated for a few minutes at a time and some designs pose additional risks associated with the containment of the radioactive material.

Other proposed stenosis treatments involve the delivery of radioisotopes directly to the wall of the stenotic vessel. The isotopes are in gas or liquid form and are delivered to the treatment site by means of a pressurized catheter. An example of such a treatment means is provided in U.S. Pat. No. 5,873,811. This approach raises questions concerning possible contamination of the operating room and radiation exposure of the operating personnel and the patient. These treatments deliver a single dose of radiation at the time of the vascular intervention.

In yet other proposed treatment means, it has been suggested that brachytherapy seeds be placed in an array adjacent to the target tissue structure. This suggestion is an outgrowth of radiation therapy plans for treating tumors. Specifically, workers have proposed arrays of seeds in a delivery-mesh or sheet that is implanted over the area of a tumor. Examples of this approach are described in U.S. Pat. Nos. 4,754,745 and 5,030,195. Because these devices incorporate a number of discrete radiation sources, they cannot be used to deliver a relatively uniform radiation dose to tubular body structures. In addition, these devices do not provide a radiation attenuation element or an integral means for shielding non-targeted tissues from radiation.

Further, U.S. Pat. No. 5,897,573 describes a suture material with a beta radiation emitting isotope specifically intended to treat stenosis that might occur at the juncture of a synthetic vascular graft and a natural vessel. Because of the radiation source described and standard vascular suturing techniques, this device and method of treatment would only be effective as a limited treatment for intimal hyperplasia in very close proximity to the suture strand. This device and treatment strategy would also not be useful in cases where the target tissue site did not require repair by suturing.

Thus, prior to the development of the present invention there has been no wrap device designed to be placed around the external circumference of a tubular body structure for the prevention of stenosis or restenosis by: delivering a radiation dose to the local target area over an extended period of time, with limited radiation exposure to operators and non-targeted tissues, that can be implanted at the time of surgery without requiring a secondary intervention and that can be safely handled during the implant procedure. Further, the devices disclosed herein include a radiation attenuation element between the radioactive surface and the target tissue in closest proximity to this surface. This design assures a far greater spatial uniformity of radiation dose to the critical wall tissues of the passageway, duct or vessel than does an intravascular source, particularly in the common case of an eccentric lesion. Many clinicians and physiologists agree that neo-intimal hyperplasia originates from cells closer to the adventitia (i.e. further from the inner wall of the vessel). Thus, circumferential device placement would position the source closer to the origin of the unwanted cellular proliferation and, thus permit lower radioactivity levels to be effective.

SUMMARY OF THE INVENTION

The current invention comprises a wrap device that is designed to be positioned circumferentially around the outside of a segment of a body tissue structure, such as a vessel, duct or passageway that has been exposed during surgery. In a preferred embodiment, the wrap is composed of three elements assembled in a layered structure: a radiation shield element, a therapeutic element and a radiation attenuation element. The wrap delivers localized, uniform radiation for the purposes of the mitigation of cellular proliferation such as intimal hyperplasia or cancer that may result from a disease process or trauma to the wall of the structure. The wrap may also be positioned adjacent to a contiguous tissue surface as in the case of a vascular bypass graft and the epicardial coronary vessel on the surface of the heart.

The therapeutic element of the wrap is a radioactive isotope that has been preferably ion implanted on a metallic substrate. The radioactive surface of the wrap is preferably positioned adjacent a shield element so as to substantially limit the radiation exposure of surrounding non-targeted tissue structures. The shield element is preferably a metallic radiation absorber such as silver or gold or a polymer filled with barium or a similar radiation absorbent material.

The element of the wrap that is positioned adjacent the target tissue structure is preferably a radiation attenuation element. The radiation attenuation element is useful to absorb radiation and thus decrease the dose differential between cells of the target tissue that are closely proximate the radiation source of the therapeutic element and cells that are more distant. This provides a more uniform, safer delivery of the intended radiation dose throughout the thickness of the target tissue structure. The radiation attenuation element is preferably made of a bio-compatible polymer material such as polyurethane and may also extend completely around the shield, so as to enclose both the radiation shield element and the therapeutic element.

The wrap can be assembled by attaching the three elements through an adhesion or lamination process. The entire wrap is then formed in such a way as to conform to the curvature of the targeted body tissue structure. The wrap may be biased through the use of specific materials or through processing conditions to retain a generally cylindrical shape. Alternatively, the wrap may be formed in the general shape of two half-cylinders that can be positioned around a target body tissue structure such as a vessel, duct or passageway. The half-cylinders can be held in a generally cylindrical shape around the tissue segment by a fastening means such as a staple or suture placed through a tab that is provided as an integral part of the radiation attenuation material or by encircling the entire device with such shape retention means. A suture clip or staple placed through the border of the radiation attenuation element or a tab integral to the radiation attenuation element can be used to anchor the wrap to at least one portion of the target tissue structure, thus maintaining the relative positions of the wrap and the target tissue structure.

These and other features of the invention will be more fully understood by reference to the following drawings.

DETAILED DESCRIPTION OF THE INVENTION

During the course of this description, like numbers will be used to identify like elements according to the different views that illustrate the invention. The term vessel is used throughout this description for simplicity; but it should be understood that this term refers to any body vessel, duct or passageway or any synthetic material used in place of such natural body tissue structure.

Figure 1:
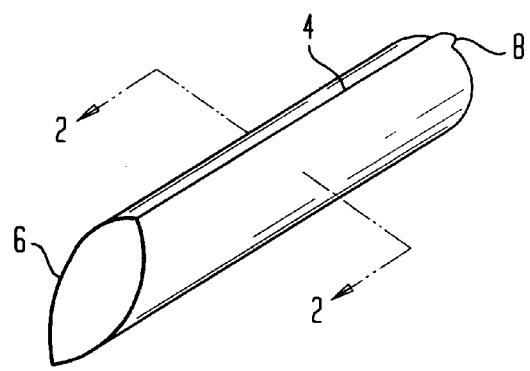
FIG. 1 is a perspective view of the wrap in the form of a longitudinally split tube with one end beveled.

Several characteristics of the invention are illustrated in the generalized design shown in perspective in FIG. 1. For the purpose of demonstrating the overall characteristics of the wrap, it is depicted here as a complete device without detailed reference to its component materials or assembly techniques. Those characteristics will be discussed later in this description. The longitudinally split tube 2 is but one example of a means by which a wrap may be placed around a vessel without incising the vessel in order to allow a continuous band to be placed around it. In the case shown, the lengthwise slit 4 may be placed at any position, but preferably along a line that represents the shortest length of the wrap. The bevel 6 at one end is designed to conform the wrap to the angle of an end-to-side juncture of a vessel with another vessel. This configuration assures that the portion of the vessel closest to the juncture can be treated over its full circumference. A tab 8 is provided near at least one end of the wrap to allow the wrap to be fastened to the vessel. The tab may be sutured, stapled or otherwise attached to the vessel; and the tab is preferably an extension of the radiation attenuation material. Fastening the tab to the vessel maintains the spatial relationship between the wrap and the vessel to assure that the treatment is delivered to the target site. The tab is preferably an extension of the radiation attenuation material so that it is not necessary to puncture the radioactive substrate of the therapeutic element in order to facilitate the attachment. This prevents radioactive material from being released into the body of the patient. In the embodiment shown, the wrap is formed in such a way as to create a mechanical bias or memory toward a cylindrical shape. This can be accomplished through the selection of materials, such as a metal with a springy or dead-bend characteristic or through processing means, as by establishing a heat induced set form.

Figure 2:
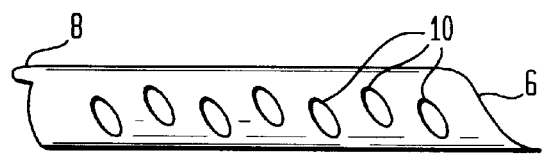
FIG. 2 is a side view of the wrap in the form of a longitudinally split tube with one end beveled and a fenestrated wall.

The general topology of the wrap can take the form of a solid material, a mesh, a knitted or woven fabric, a felt or a film. The intended location, shape and use will partially determine the topology, for example, a mesh will allow for ingress and egress of tissue fluids and cells to and from the outer surface of the vessel The wrap depicted in FIG. 2 is a side view of the device shown in FIG. 1 with the exception that the wrap is fenestrated 10 through its full thickness. The fenestrations may be random or may be in a regular pattern. The fenestrations allow for the ingress and egress of tissue fluids and cells to and from the outer surface of the vessel. In certain applications, such as in the case of relatively long wraps, it may be desirable to incorporate such fenestrations in the wrap.

Figure 3:
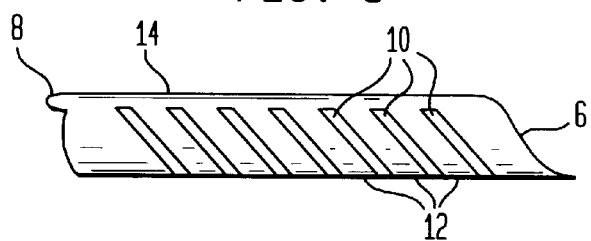
FIG. 3 is a side view of the wrap in the form of a longitudinally split tube with one end beveled and fenestrated so as to allow longitudinal flexibility.

In the embodiment illustrated in FIG. 3 the wrap has regular or symmetric fenestrations. This figure shows a fenestrated wrap that has been formed in the shape of a longitudinally split tube. The wall of the tube is interrupted by multiple fenestrations 10 placed in a circumferential direction, but not necessarily at right angles to the longitudinal axis of the tube. The ribs 12 formed by the portion of the wrap remaining are connected to each other by a spine 14 section of the wrap that is adjacent each side of the longitudinal split. The resulting structure allows for the ingress and egress of tissue fluids and cellular material and also permits a degree of flexibility along the longitudinal axis. Although the flexibility is not equal in all directions it is of value when the tissue structure within the wrap is not in a fixed position in the body or when the structure is relatively long and not completely straight over the length being treated.

Figure 4:
FIG. 4 is a side view of the wrap in the form of a band shaped into a spiral tube.

The wrap may have a number of different configurations, including a longitudinally split tube, a spiral band, a flat, formable band, continuous coil, an interrupted coil, a sheet, or a fenestrated band, for example. A spiral band configuration is shown in FIG. 4 in the form of a band wound about a central axis in the form of a spiral 16. A spiral band wrap may be placed around a vessel without incising the vessel in order to allow a continuous band. The spiral wrap may also incorporate a tab 8 near at least one end of the wrap to allow the wrap to be fastened to the vessel. This configuration offers a good degree of flexibility in all directions along the longitudinal axis.

Figure 5:
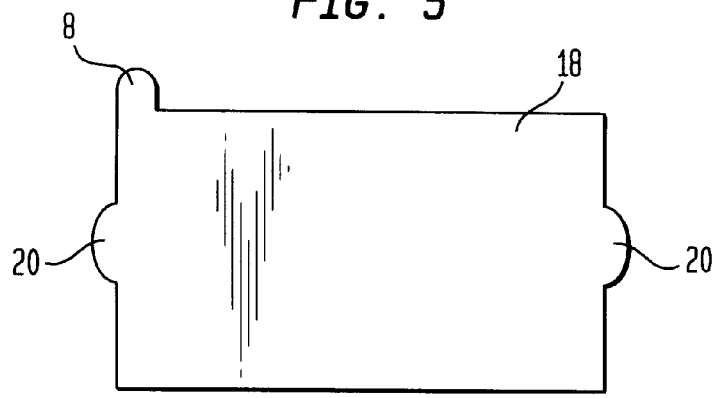
FIG. 5 is a top view of the wrap in the form of a flat band.

A flat band configuration 18 is shown in FIG. 5. The band is not preformed or biased in the shape of a cylindrical structure, but may be wrapped around such a structure at the time of implant. The band incorporates a tab 8 near at least one end of the wrap to allow the wrap to be fastened to the vessel. The band also incorporates at least two additional tabs 20. These tabs are opposed when the band is placed around the target tissue site and are fastened to each other by suturing, stapling or the like to hold the wrap in its circumferential position around the vessel. The tabs also are preferably an extension of the radiation attenuation material so that it is not necessary to puncture the radioactive carrier in order to facilitate the attachment of the band to itself.

Figure 6:
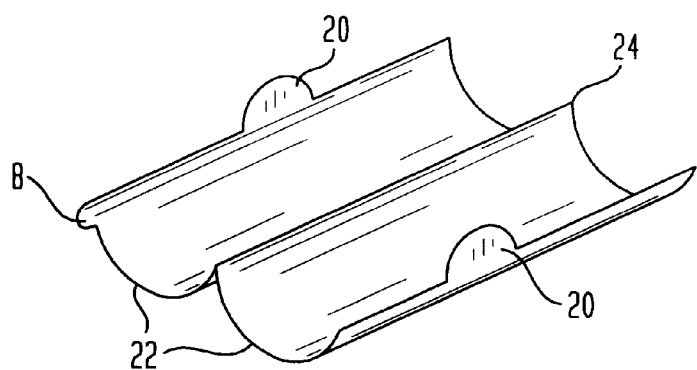
FIG. 6 is a perspective view of the preferred embodiment of the wrap in the form of a hinged, longitudinally split tube.

A preferred embodiment is the split tube configuration, illustrated in FIG. 6. The wrap is provided in the form of two hemi-cylinders 22 with at least one self-attachment tab 20 positioned at the edge of each half. At least one additional tab 8 is provided near at least one end of at least one hemi-cylinder to allow the wrap to be fastened to the vessel. The two halves are preferably joined together by extending the radiation attenuation material over both halves forming a flexible hinge 24 at the side opposite the self-attachment tabs. This preferred design can be applied around the vessel with the use of standard surgical tools such as grasping instruments or hemostats, thus allowing the wrap to be readily positioned and held at the intended target site while the self-attachment tabs are fastened together by means of a suture, clip or other fastening device. There is no need for specialized instruments to open the wrap for positioning around the target tissue structure and it is relatively easy to adjust the position of the wrap once it has been placed around the target tissue.

Figure 7:
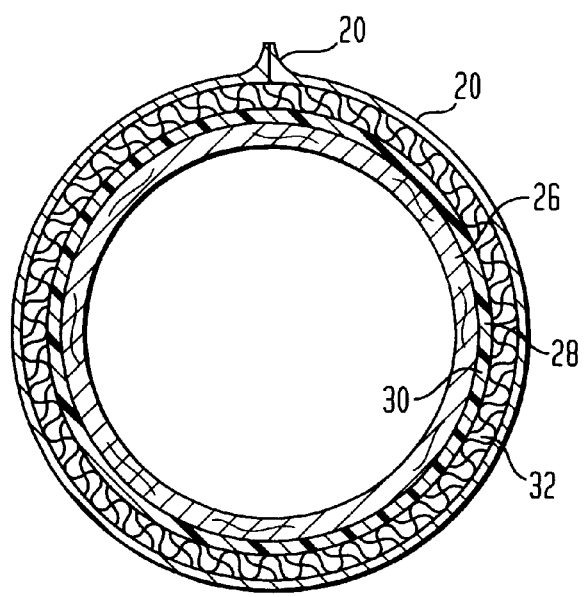
FIG. 7 is an end view of the preferred embodiment of the wrap encircling a tubular body structure.

A cross section of an end view of a preferred embodiment of the wrap in position around a vessel is shown in FIG. 7. The vessel 26 is shown to be in intimate contact with the radiation attenuation element 28. The radiation attenuation element completely covers the radiation bearing substrate 30 and may also cover the outer surface of the shield 32. Also shown are the self attachment tabs 20.

Figure 8:
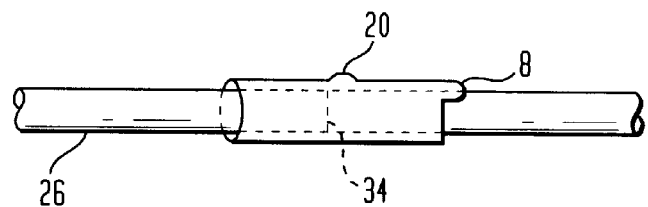
FIG. 8 is a side view of the preferred embodiment of the wrap positioned around a tubular body structure.
Figure 9:
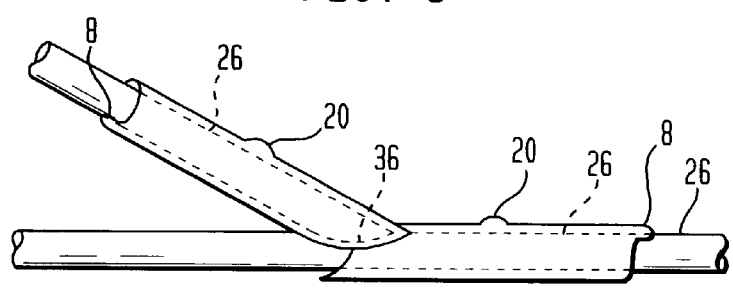
FIG. 9 is a side view of the wrap positioned at the site of an end-to-side anastomosis of a synthetic vascular graft and a natural vessel.

The wrap can be fabricated for use on a variety of body tissue structures and for a variety of therapeutic objectives. For example, a wrap can be positioned at the site of an end-to-end anastomosis 34 of a natural vessel and a synthetic graft as illustrated in FIG. 8. Two segments of the wrap can be used together and positioned at the site of an end-to-side anastomosis 36 of a natural vessel and a synthetic graft as in the case of an arteriovenous dialysis access graft as illustrated in FIG. 9.

Figure 10:
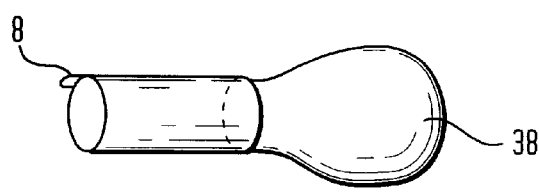
FIG. 10 is a bottom view of the wrap with a flattened, broad end designed to be at the site where a coronary vascular graft is joined to a natural epicardial vessel.
Figure 11:
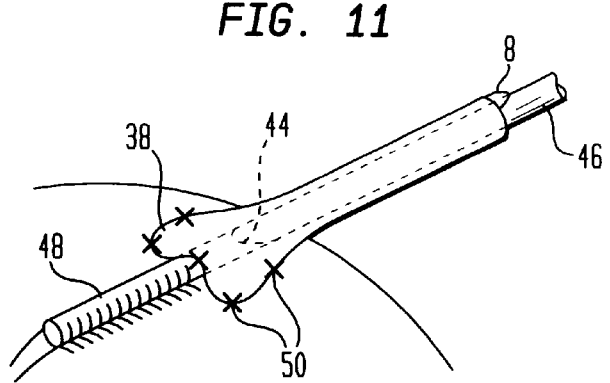
FIG. 11 is a perspective view of the wrap of FIG. 9 placed at the anastomosis of a natural or synthetic coronary vascular graft and a natural epicardial vessel.

The wrap can be configured to provide for a non-cylindrical extension to cover non-cylindrical body tissue adjacent a cylindrical body tissue or synthetic material structure. For example, the wrap can be configured to be positioned adjacent to a contiguous tissue surface as in the case of a vascular bypass graft and an epicardial vessel on the surface of the heart. The use of such an extension is illustrated in FIGS. 10 and 11. While the body of the wrap extends completely around the circumference of the distal segment of the natural vessel or graft, one end of the wrap 38 is extended to a tongue-like shape that may be sutured to the surface of the epicardium or other contiguous tissue surface. The wrap can be positioned at the site of an anastomosis 44 of a natural or synthetic coronary artery bypass graft 46 and an epicardial segment of a natural coronary artery 48. The wrap is held in position by means of sutures 50 placed at the periphery of the flattened end of the wrap as it lies in intimate contact with the epicardium.

The wrap can be constructed using materials and processes well known in the art. The shielding element is generally less than 2 mm in thickness and preferably should absorb at least 95% of the energy that would otherwise be allowed to reach non-targeted tissue structures outside of the wrap. The shielding element is preferably comprised of a flexible, crush-resistant, bio-safe material. In one preferred embodiment, the shield is comprised of an efficient radiation absorbing material, such as silver, gold or barium filled polymer. In an alternate embodiment the shield element is not used, for example, when the radioactive isotope in the therapeutic element has a very low activity, when the wrap will be placed in a deep body location, or when some outward radiation is desired.

Figure 12:
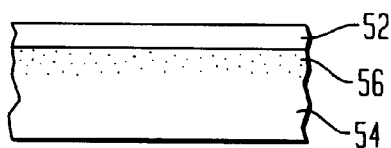
FIG. 12 is a magnified schematic representation of a cross-section of one wall of the wrap.

In the design illustrated in FIG. 12, the radioactive isotope 56 is placed directly on one surface of the shield 54 material. The radioactive isotope is covered with a radiation attenuation material 52 that prevents direct contact between the isotope and the target tissue structure. The radiation attenuation element is preferably a polymer that is relatively resistant to radiation damage such as a polyurethane material. The radiation attenuation material is generally less than 2 mm in thickness and is intimately in contact with the isotope so as to provide a barrier to possible leakage of isotope into the body of the patient. The radiation attenuation material serves as an absorber of low energy radiation and diminishes the dose gradient between those target cell structures closest to the isotope source and those somewhat further from the isotope source. This element thus facilitates delivery of a more uniform dose throughout the tissue depth than might otherwise be achieved.

Figure 13:
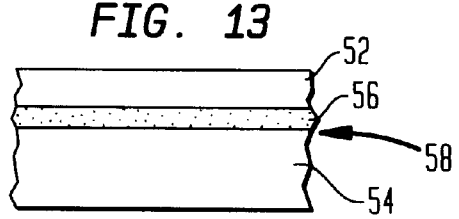
FIG. 13 is a magnified schematic representation of an alternate design of a cross-section of one wall of the wrap.

In the preferred embodiment depicted in FIG. 13, the radioactive isotope 56 is placed on a high-purity thin metal foil substrate 58, preferably by ion implantation techniques. By variations of these techniques it is possible to provide differing levels of radioactivity at different positions on the surface of the wrap. It is also possible to implant ions that will produce more than one radiation source or isotope and both beta and gamma sources simultaneously. The ion implantation process will allow non-radioactive precursor isotope(s) to be activated in a nuclear reactor. The metal foil substrate is preferably a very pure, non-activatable, low atomic number material in order that it that will not produce substantial quantities of unwanted radiation when placed in the reactor.

It is also a feature of this invention that more than one radioactive substrate can be incorporated in the wrap in order to increase total dose or to provide a treatment with radiation delivered simultaneously from more than one source. The isotope can be incorporated into the substrate, placed upon the substrate or both. The substrate elements(s) can then be assembled to the shield element 54, preferably with the radioactive surface toward the shield. The assembly of the wrap can be accomplished using methods well known in the art, particularly for producing laminated structures. This assembly method provides a barrier to minimize possible leakage of isotope into the body of the patient. The radiation attenuation material 52 is placed in intimate contact with the non-activated surface of the radioactive substrate and sealed to the substrate element with an adhesive, through heat-sealing or via a molding process.

The radiation attenuation element 52 prevents direct contact between the isotope and the target tissue structure. The radiation attenuation element is preferably comprised of a flexible polymer that is relatively resistant to radiation damage such as a polyurethane material. Preferred polymers should have essentially the same radiation absorption characteristics of body tissue. The radiation attenuation element is generally less than 2 mm in thickness. The radiation attenuation element serves as an absorber of any low energy radiation resulting from impurities in the substrate and diminishes the dose gradient between those target cell structures closest to the isotope source and those further from the isotope source. The radiation attenuation element thus facilitates delivery of a more uniform dose throughout the tissue depth than might otherwise be achieved.

Both the radioactive isotopes used, and the thickness and composition of the attenuation component can be adjusted to vary the radiation dose delivered. In a preferred embodiment, the dose of radiation delivered to the tissue to be treated is between 10 and 200 Gy when measured at a tissue depth of about 2 millimeters.

Figure 14:
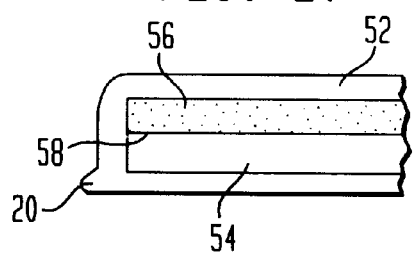
FIG. 14 is a magnified schematic representation of a preferred embodiment of a cross-section of one wall of the wrap.

In a preferred embodiment of the wrap, illustrated in FIG. 14, the radioactive isotope preparation, substrate configuration and shield/substrate assembly are as illustrated in FIG. 13, but the radiation attenuation component is formed entirely around all surfaces and the exposed edges of the shield/substrate assembly. The only areas not covered by the radiation attenuation material are the fenestrations, if present. In addition to the advantages discussed previously, this configuration of the radiation attenuation element also serves to assure that the wrap presents a uniform biocompatible polymer surface to all contacted body tissues. Extending the radiation attenuation element beyond the edges of the shield/substrate assembly provides material for the self-attachment tab 20 and the vessel anchoring tab shown in FIG. 6. Such encapsulation of the shield/substrate assembly also serves as an additional barrier to minimize the possibility of leakage of the radioactive isotope into the body of the patient.

Figure 15:
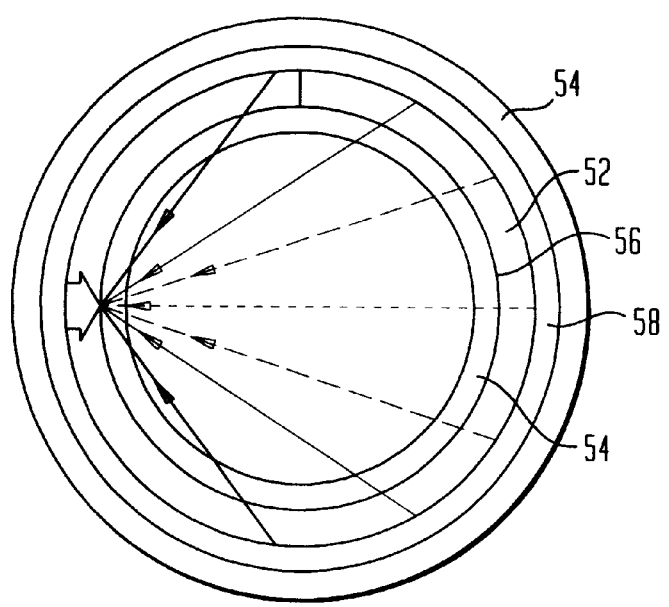
FIG. 15 is a schematic illustration representing how the radiation dose delivered to any given tissue site within the wrap is the integrated sum of the activities delivered from each point on the encircling wrap.

The cylindrical configuration of a preferred, installed wrap allows for lower levels of radiation to be used in the therapeutic element because of the additive effect of the radiation to the target tissue. FIG. 15 illustrates this principal in a schematic representation of the wrap placed around a vessel. Several arrows are shown emanating from the radioactive isotope and directed toward a point at the surface of the vessel. These arrows illustrate that the radiation dose delivered to a given point on or within the targeted tissue structure is calculated as the integrated summation of contributed radiation from all points within the cylindrical wrap. Because radiation is delivered to the encircled tissue structure from all directions, the wrap design allows a reduction in the radioactive load density per unit area on the radioactive surface of the wrap. Thus the safety of the device is enhanced relative to an intravascular radiation source or a flat source where the radiation delivered to a given tissue target is delivered nearly entirely from a point on the device immediately adjacent to the target tissue. Also, because the great majority of the radiation emitted by the present invention is directed inward, the device requires less shielding during shipping and it presents lower exposure risk during handling by health-care personnel.

One example of a preferred wrap is prepared using a pure aluminum foil substrate as the target for implantation of non-radioactive Xenon ions. The foil is less than about 0.005 inches thick. Xenon 124 and silicon are co-deposited into the foil using methods known in the art. The Xenon implanted aluminum foil is then activated by placing it in a nuclear reactor where the Xenon is converted primarily to Iodine-125. The activated foil is then positioned with the radioactive surface adjacent to silver radiation shielding material having a thickness of less than about 0.040 inches. The shield element thickness is selected so as to absorb at least 90% of the radiation emitted from the radioactive side of the substrate. The substrate and shield are then enclosed in a polyurethane radiation attenuation material. The tissue facing side of the radiation attenuation element is less than about 0.040 inches thick and the outward facing surface is less than about 0.020 inches thick. The radiation attenuation element may be sealed to the substrate/shield assembly and itself by means of an adhesive. Other wraps are made using heat-sealing as well as "potting" or molding with the polymer in liquid form. Portions of the radiation attenuation material are extended beyond the edges of the shield material so as to allow for the formation of tabs which permit the completed wrap to be fastened to the body structure and to itself. The device is then formed into a cylindrical shape by mechanically pressing the wrap around a mandrel.

In a second example, a second silicon layer, generally less than 0.001 inch thick is placed on top of the co-deposited xenon/silicon layer. This additional layer further minimizes the possibility that radioactive material will leak into the body of the patient.

In a third example, the aluminum foil substrate is replaced by a thin flexible fabric produced from highly pure silica yarns and the silver shield material is replaced by a barium filled polymer shield material. This configuration results in a somewhat more flexible wrap.

In a fourth example, the substrate consists of a very thin layer of highly pure carbon material. This embodiment allows reduction of the overall thickness of the device.

The design of the wrap allows for multiple methods of varying the energy and dose level of the radioactivity. A source of ionizing radiation may be selected from the range of beta and gamma producing isotopes based on the desired energy level and half-life for the planned therapeutic treatment. Isotopes may be applied through traditional radiochemistry techniques or through ion implantation techniques. Multiple isotopes may applied to the same radiation substrate or multiple substrates may be plied together to achieve the desired therapeutic combination of energies, dose rates, total activity and treatment duration. The thickness of the radiation attenuation element can be varied to selectively absorb unwanted low energy activity and to decrease the radiation dose gradient through the thickness of tissue being treated.

While the invention has been described with reference to its use in the treatment of vascular disease, such as excessive intimal hyperplasia, it will be appreciated by those familiar with a broad range of medical treatment modalities, that the invention can be used, for example, as a post-operative or prophylactic treatment for cancer or other diseases of generally tubular body structures. It should also be evident to those skilled in the art that modifications can be made to parts of the invention and to the fabrication procedures without departing from the intent and scope thereof.

What is claimed:

1. A device for inhibiting the growth or mitigating the extent of disease or undesirable proliferation of cells through the localized delivery of radiation to a natural or synthetic target tissue, comprising one or more substrate layers each layer having at least one source of radiation, and one or more shielding layers arranged adjacent to said one or more substrate layers, wherein said radiation source is comprised of one or more radioactive isotopes, and whereby said one or more shielding layers limits the radiation radiated from said one or more radiation layers through said one or more shielding layers.

2. The device of claim 1 wherein said at least one source of radiation is incorporated using a method selected from the group consisting of ion implantation, neutron bombardment, alloying, solid state diffusion, liquid diffusion and solution dispersion.

3. The device of claim 1, further comprising one or more radiation attenuation layers adjacent to said one or more substrate layers, wherein said one or more attenuation layers absorb a portion of the radiation from said radiation source thereby diminishing the radiation dose gradient between that part of the target tissue in very near approximation to the radiation source and that part of the target tissue that is somewhat further from said radiation source.

4. The device of claim 1, wherein said one or more substrate layers are comprised of a material selected from the group consisting of metal, carbon, silica, polymer, collagen, cotton, and combinations thereof.

5. The device of claim 1, wherein said device has a generally cylindrical or tubular geometry.

6. The device of claim 1, wherein said device is in the form selected from the group consisting of a continuous coil, an interrupted coil, a sheet, a band, a fenestrated band and split tube.

7. The device of claim 1 further comprising an attachment means for attaching the device in a location near said target tissue.

8. The device of claim 7 wherein said attachment means is secured using suturing or stapling.

9. The device of claim 1 wherein the device is in the form selected from the group consisting of a solid material, a mesh, a knitted or woven fabric, a felt and a film.

10. A device for inhibiting the growth or mitigating the extent of disease or undesirable proliferation of cells through the localized delivery of radiation to a natural or synthetic target tissue, comprising one or more substrate layers each layer having at least one source of radiation, wherein said radiation source is comprised of one or more radioactive isotopes, and wherein the total dose of radiation delivered to tissue is between 10 and 200 Gy at a depth of 2 millimeters.

11. The device of claim 10 wherein the radioactive half-life of said one or more isotopes is between 2 days and 100 days.

12. The device of claim 10 wherein said radiation source radiates gamma radiation, beta radiation, or a combination thereof.

13. The device of claim 10 wherein said radioactive isotopes are deposited on said one or more substrate layers.

14. The device of claim 10 wherein said radioactive isotopes are incorporated in said one or more substrate layers.

15. The device of claim 10 wherein said one or more radioactive isotopes are distributed in a pattern thereby varying the radiation levels at different points on said one or more substrate layers.

16. A method for inhibiting the growth or mitigating the extent of disease or undesirable proliferation of cells in a natural or synthetic target tissue, comprising delivering a localized dose of radiation to said target tissue using the device of claim 1.

17. The method of claim 16 wherein said target tissue is selected from the group consisting of a natural or synthetic body passageway, a natural or synthetic body duct and a natural or synthetic blood conduit.

18. The method of claim 17 wherein said device is wrapped completely or partially around said target tissue.

* * * * *